Figure 1:
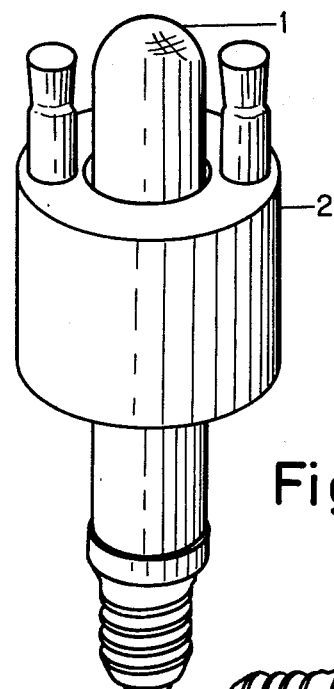

United States Patent [19]

Kloosterboer et al.

[11] 4,080,169
[45] Mar. 21, 1978

[54] DETERMINATION METHOD FOR MERCURY IN ORGANIC COMPOUNDS

[75] Inventors: Johan G. Kloosterboer; Antoinetta M. Kiemeneij, both of Eindhoven, Netherlands

[73] Assignee: U.S. Philips Corporation, New York, N.Y.

[21] Appl. No.: 698,528

[22] Filed: Jun. 22, 1976

[30] Foreign Application Priority Data

Jul. 22, 1975 Netherlands .......................... 7508712

[51] Int. Cl.² ...................... G01N 21/24; G01N 33/18
[52] U.S. Cl. ............................. 23/230 R; 250/432 R
[58] Field of Search ........ 23/230 PC, 253 PC, 230 R; 250/432, 433, 434, 435, 436, 437, 438

[56] References Cited

U.S. PATENT DOCUMENTS

| | | | |
|---|---|---|---|
| 1,190,609 | 7/1916 | Von Recklinghausen | 250/432 |
| 1,473,095 | 11/1923 | Henri et al. | 250/435 X |
| 2,291,574 | 7/1942 | Gleason et al. | 250/436 |
| 2,935,611 | 5/1960 | Myers | 250/435 |
| 3,628,010 | 12/1971 | Oberwil et al. | 250/432 X |
| 3,826,618 | 7/1974 | Capuano | 23/232 R |

*Primary Examiner*—Robert M. Reese
*Attorney, Agent, or Firm*—Frank R. Trifari; Carl P. Steinhauser

[57] ABSTRACT

Photolysis of organic mercury compounds in mercury-containing samples to determine mercury therein by means of irradiation with a light source emitting predominantly below 260 nm.

1 Claim, 3 Drawing Figures

DETERMINATION METHOD FOR MERCURY IN ORGANIC COMPOUNDS

The invention relates to a method of determining mercury in organic compounds and to an apparatus for carrying out the determination. The invention relates in particular to a method of determining mercury in behalf of environmental control.

Many methods are known of determining ionogenic mercury, for example, spectrophotometrically after reaction with dithizon, neutronactivating analysis, spectrophotometrically by atomic absorption of mercury after reduction to Hg° and transferring to the vapour form, and so on. The latter method is to be preferred due to its simplicity and sensitivity.

However, in many organic mercury compounds said mercury is bound so strongly that it cannot easily be converted into ionogenic mercury. In natural waters, for example, $CH_3Hg^+$ ions and also the compound $(CH_3)_2Hg$ are formed from $Hg^{++}$ ions after some time which cannot be reduced to $Hg^0$ even by the strong reducing point $Sn^{2+}$. As is stated in literature (L, Magos, Analyst 96, 847 (1971)), these substances which are least stable of the organic mercury compounds can be reduced indeed in a large excess of a mixture of $CdCl_2$ and $SnCl_2$ in initially strong acid and then strongly alkaline medium.

In general, destruction of organic mercury compounds can be carried out chemically by means of very strong oxidants, for example, $K_2Cr_2O_7$—$H_2SO_4$ or $HNO_3$—$HClO_4$, after which, in the case of detection by means of atomic absorption spectrophotometry, the formed $Hg^{2+}$ ions have to be reduced to elementary mercury. These methods of destruction are rather complicated and timeconsuming. The large quantity of chemicals gives rise to high blank values and the required heating easily leads to loss of volatile mercury compounds.

From a technical bulletin (No. 27) of the Inland Waters Branch of the Department of Energy, Mining and Resources, Ottawa 1970 by P. D. Goulden and B.K. Afghan, a photochemical method is known for the destruction of organic mercury compounds. After the addition of acids ($HNO_3$ + $H_2SO_4$) and an oxidant ($H_2O_2$) the sample is thus decomposed by irradiation with a mercury vapour lamp of medium high pressure, the mercury becoming available as ionic mercury. Such mercury vapour lamps consume a rather high power (for example 550 W) in which, due to the low efficiency, rather long irradiation times are still necessary (for example 2 hours). So much heat is developed that precautions have to be taken to cool the samples so as to prevent losses of mercury.

When the mercury is to be determined by means of atomic absorption measurement, the ionic mercury obtained after photolysis must be reduced into elementary mercury by reduction. This can be carried out simplest by means of the addition of an $SnCl_2$-HCl solution.

According to the invention it has been found that a very effective photolysis of solutions of organic mercury compounds is achieved with an irradiation source having a considerable portion of the emission in the part of the ultraviolet spectrum which lies below 260 nm. It was established that the addition of HCl then is sufficient. In addition oxidants are superfluous.

The low-energetic radiation sources to be considered for this purpose are inter alia a 12 W low pressure mercury lamp, a 16 W cadmium lamp, a 16 W zinc lamp, a 75 W combined ZnCdHg lamp or even a 5.5 W low pressure mercury lamp.

Because between 260 and 200 nm the molar extinction coefficient of most organic mercury compounds is rather high and because in addition the quantum efficiency for the decomposition of these compounds as a rule increases with decreasing wavelength, the use of these lamps results in considerably shorter irradiation times.

When in addition to the mercury compounds to be photolysed few other substances absorbing in the said spectral region occur, lowpower lamps generally suffice. When, however, as may be the case with surface water a strong background absorption occurs it is of advantage to perform the irradiation with a combined ZnCdHg lamp as mentioned above.

Figure 2:
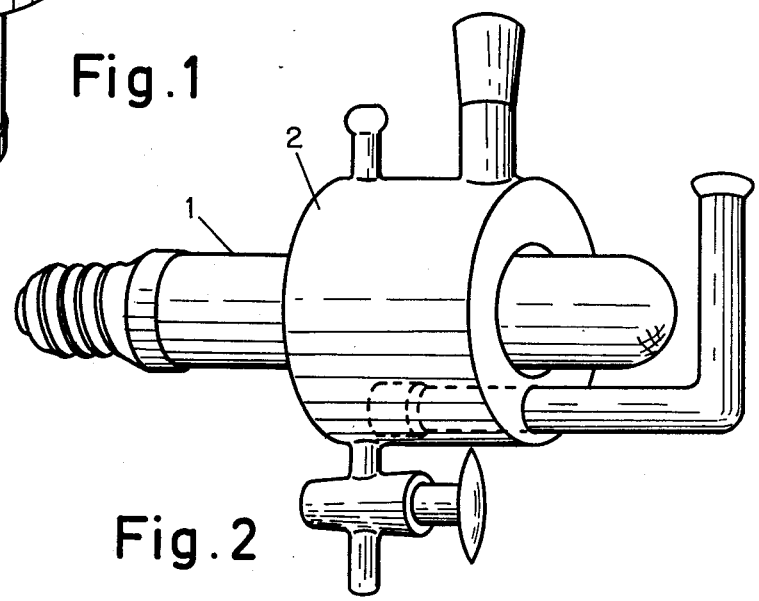
Figure 3:
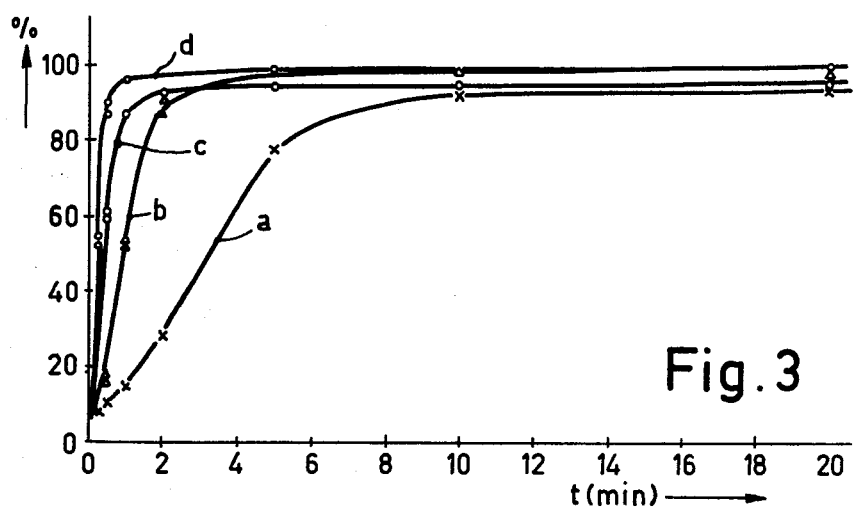

The invention will be described with reference to the accompanying drawing in which:

FIGS. 1 and 2 show a cell for liberating mercury in organic mercury compounds; and FIG. 3 shows a comparison of irradiation results in liberating mercury from standard solutions of methyl mercury chloride as a function of irradiation time.

For the analyses which are described hereinafter for illustration of the invention, the above-mentioned spectral lamps were used which are marketed as type numbers Philips' 93109, 93107, 93106 and 93146 and Pen-Ray 11-SC-1. These lamps 1 were used in combination with a quartz glass toroidal cell 2 as shown in one of the FIGS. 1 and 2 of the accompanying drawing in which the height of the cylinder is 40 mm, the diameter 70 mm and the hole diameter is 33 mm. The wall thickness is 1.5 mm. The cells are surrounded by a cooling jacket which, however, is not shown in the drawing. In this embodiment the absorption of radiation by the sample present in the cell is considerably increased as compared with the usual arrangement of a cell in front of the lamp. The construction shown in FIG. 2 has the advantage tht the cell may also be used to perform a reduction reaction in it, after which, by leading through said cell a gas, for example air, the formed $Hg^0$ can be transferred to an optical cell arranged in the light path of the atomic absorption spectrophotometer. A further advantage is when the outer wall of the cell is provided with a reflecting layer, for example an aluminum layer. In practice said layer is still provided with a protective layer, for example $SiO_2$ or lacquer.

FIG. 3 shows for comparison the irradiation results in percent of liberated mercury from standard solutions of methyl mercury chloride as a function of the irradiation time in minutes. This is shown for a 12 W mercury lamp (a), a 16 W Cd lamp (b), a 16 W Zn lamp (c) and a 75 W ZnHgCd lamp (d).

A few examples of determinations will now be described to explain the invention.

EXAMPLE I

Water from the river Waal was acidified to 0.25 M with HCL immediately after taking the samples and then 100 ml hereof were irradiated for 10 minutes with the combined ZnCdHg lamp in a cell as shown in FIG. 2 0.5 ml of 10% $SnCl_2$ solution in 1 M HCl was then added to the sample and air was led through, with which the formed atomic mercury was conveyed to an optical cell. The atomic absorption of Hg in said optical cell was measured by means of a Pye-Unicam SP 1900 AA spectrophotometer.

In order to verify the efficiency of the photolysis a number of samples were subjected to a wet-chemical destruction method (S.H. Omang, Anal. Chem. Acta 53, 415 (1970)). They were treated according to this method for 20 hours with 2 or 4% $KMnO_4$. A part of the samples were then evaporated from 1 liter to 60 ml, diluted with water and measured to establish the fact that no loss of mercury occurs during the evaporation. Another part was also evaporated and heated for 20 minutes at 120° C in a teflon bomb with HF (38–40%), HCl and $HNO_3$ according to a known method (S.H. Omang and P.E. Paus, Anal. Chem. Acta 56, 393 (1971)). After cooling and opening the bomb, the HF was complexed with boric acid. The formed $Hg^{2+}$ was then determined in the above-described manner.

In the following table the analysis results of the photolysis method are compared with those of the wet-chemical destruction. In brackets are stated the measured values of blank determinations. The quantity of mercury is denoted in $\mu g/l$. The blank has already been subtracted from the measured values. The table supports the equivalence of photolytic and wet-chemical destruction.

TABLE

| Sample treatment | | analysis result (Hg in $\mu g/l$) | |
|---|---|---|---|
| unirradiated | | 0.31 | |
| irradiated with ZnCdHg lamp | 10 min. | 1.01 | 1.00 |
| irradiated with ZnCdHg lamp | 30 min. | 1.15 | 1.11 |
| | | 1.05 | 1.12 |
| treated with $KMnO_4$; | 2% $KMnO_4$ | 0.98(0.06) | 1.02(0.03) |
| | 4% $KMnO_4$ | 1.04(0.08) | 0.97 |
| treated with $KMnO_4$ evaporated and diluted; | | 1.07 | 1.01 |
| | 2% $KMnO_4$ | 1.00(0.24) | 1.06(0.23) |
| | 4% $KMnO_4$ | 1.07(0.27) | 1.06(0.31) |
| treated with $KMnO_4$ evaporated heated in teflon bomb and diluted: | | | |
| | 2% $KMnO_4$ | 1.12(0.38) | 0.99(0.39) |
| | 4% $KMnO_4$ | 1.08(0.42) | 1.09(0.43) |

EXAMPLE II 100 ml of a solution which contained up to $10\mu g/l$ of the very stable diphenylmercury was acidified in the manner stated in Example I to 0.25 M with HCl and transferred to an irradiation cell as shown in FIG. 1. The solution was irradiated with a zinc lamp (type 93106) for 10 minutes after which the formed ionic mercury was determined by means of an atomic absorption spectrophotometer. More than 98% of the mercury present in the original solution was recovered.

EXAMPLE III

A soil sample was aerated in the manner described in literature (Y. Kimura and V. L. Miller, Anal. Chem. 32, 420 (1960)). The volatile organic mercury compounds dragged along in the air stream were caught in a wash bottle which contained an aqueous phosphate solution.

100-ml-samples were taken at regular intervals from the phosphate solution and after acidification in the manner described in Example I, mercury was determined therein. After taking each sample, the phosphate solution was made up to the original volume. After no mercury was found, the aeration was discontinued and the sum of the results of all determinations was related to the quantity of soil sample so as to obtain the content of mercury in the form of volatile organic compounds.

EXAMPLE IV

A fish sample of 10 g was homogenized in water to which HCl had been added in the manner described in literature (G. Westhoo, Acta Chem. Scand. 20, 2131 (1966)). The liquid was extracted with dichloromethane. The extract was transferred to a cell as shown in FIG. 2 and completed with water. By leading through gas the dichloromethane is removed.

The resulting aqueous solution was irradiated and analysed in the manner described in Example I.

What is claimed is:

1. A method of determining mercury in samples in which at least a part of the mercury is bound in organic compounds comprising the steps of acidifying a solution containing said mercury compounds with HCl, irradiating said compounds with radiation from a source having a considerable portion of the emission in the part of the ultraviolet spectrum which lies below 260 nm to liberate said bound mercury from the compounds by photolysis, and thereafter determining the mercury in the form of the ion or after reduction in the elementary form of the metal.

* * * * *